United States Patent [19]

Hieftje et al.

[11] Patent Number: 4,800,279

[45] Date of Patent: Jan. 24, 1989

[54] METHODS AND DEVICES FOR NEAR-INFRARED EVALUATION OF PHYSICAL PROPERTIES OF SAMPLES

[75] Inventors: Gary M. Hieftje, Bloomington, Ind.; David E. Honigs, Brier, Wash.; Thomas B. Hirschfeld, Livermore, Calif.

[73] Assignee: Indiana University Foundation, Bloomington, Ind.

[21] Appl. No.: 776,133

[22] Filed: Sep. 13, 1985

[51] Int. Cl.$^4$ ............................................. G01J 1/00
[52] U.S. Cl. ................................... 250/339; 250/255
[58] Field of Search ............... 250/338, 339, 341, 255; 356/311, 318, 319, 320

[56] References Cited

U.S. PATENT DOCUMENTS

| | | | |
|---|---|---|---|
| 4,323,777 | 4/1982 | Baskins et al. | 250/339 |
| 4,433,239 | 2/1984 | Thompson | 250/339 |
| 4,591,718 | 5/1986 | Amer | 250/339 |

OTHER PUBLICATIONS

Lebedev, V. P.; Miroshnichenko, E. A.; Matyushin, Y. N.; Larinov, B. P.; Romanov, V. S.; Bukolov, Y. E.; Denisov, G. M.; Balepin, A. A.; Lebedev, Y. A., *Zh. Fiz. Khim*, (1975), pp. 1928–1932.

American Society for Testing and Materials, "Standard Method of Test for Molecular Weight of Petroleum Oils from Viscosity Measurements", *Annual Book of ASTM Standards*, (1973), pp. 847–850.

Wetzel, David L., "Near-Infrared Reflectance Analysis", *Analytical Chemistry*, vol. 55, No. 12, (Oct. 1983), pp. 1165 A–1166 A, 1168 A, 1170A, 1172A, 1174A, 1176A.

Watson, C. A., "Near Infrared Reflectance Spectrophotometric Analysis of Agricultural Products", Analytical Chemistry, vol. 49, No. 9 (Aug. 1977), pp. 835 A–840 A.

Starr, C.; Smith, D. B.; Blackman, J. A.; Gill, A. A., "Applications of Near Infrared Analysis in Breeding Wheats for Bread-Making Quality", *Anal. Proc.*, vol. 20, (1983), pp. 72–74.

Winch, J. E.; and Major, H., "Predicting Nitrogen and Digestability of Forages Using Near Infrared Reflectance Photometry", *Can. J. Plant Sci.*, vol. 61, (Jan. 1981), pp. 45–51.

Norris, K. H.; Barnes, R. F.; Moore, J. E.; Shenk, J. S., "Predicting Forage Quality by Infrared Reflectance Spectroscopy", *Journal of Animal Science*, vol. 43, No. 4, (1976), pp. 889–897.

Rose, John J., "Analysis of Parenteral Drugs by NIRA", The Pittsburgh Conference, Atlantic City, N.J., (Mar. 1983), Paper 707.

Honigs, D. E.; Heiftje, G. M.; Hirschfeld, T., "A New Method for Obtaining Individual Component Spectra from Those of Complex Mixtures", *Applied Spectroscopy*, vol. 38, No. 3, (1984), pp. 317–322.

Honigs, D. E.; Freelin, J. M.; Hieftje, G. M.; Hirschfeld, T. B., "Near-Infrared Reflectance Analysis By Gauss--Jordan Linear Algebra", *Applied Spectroscopy*, vol. 37, No. 6, (1983), pp. 491–497.

Weast, R. C. and Astle, M. J., Eds., *CRC Handbook of Chemistry and Physics*, 60th ed., (1979), pp. D-82 to D-84, [Table of Values of Chemical Thermodynamic Properties of Hydrocarbons].

(List continued on next page.)

*Primary Examiner*—Janice A. Howell
*Attorney, Agent, or Firm*—Kirkland & Ellis

[57] ABSTRACT

Methods are disclosed for quantifying physical properties of gaseous, liquid or solid samples. The near-infrared absorbance spectra of a representative field of calibration samples are measured and recorded using a spectrophotometer. The absorbance spectra of the calibration samples are evaluated by a row-reduction algorithm to determine which wavelengths in the near-infrared spectrum, and associated weighting constants, are statistically correlated to the physical property being quantified. The near-infrared absorbance of actual samples is then measured at each of the correlated wavelengths, and then corrected by the corresponding weighting constants. A reference value for the physical property being quantified is then computed from the corrected measure of the absorbance of the sample at each of the correlated wavelengths.

23 Claims, 3 Drawing Sheets

OTHER PUBLICATIONS

Goddu, Robert F. and Delker, Dorothy A., "Spectra-Structure Correlations for the Near-Infrared Region", *Analytical Chemistry*, vol. 32, No. 1, (Jan. 1960), pp. 140–141.

Kaye, Wilbur, "Near-Infrared Spectroscopy—I. Spectral Identification and Analytical Applications", *Spectrochimica Acta*, vol. 6, (1954), pp. 257–287.

Whetsel, K. B., "Near-Infrared Spectrophotometry", *Applied Spectroscopy Reviews*, vol. 2(1), (1968), pp. 1–67.

Hirschfeld, T. and Stark, E., "Near-Infrared Reflectance Analysis of Foodstuffs", *Analysis of Foods and Beverages*, Chakrabarty, E., Ed., (1984), pp. 505–551.

METHODS AND DEVICES FOR NEAR-INFRARED EVALUATION OF PHYSICAL PROPERTIES OF SAMPLES

BACKGROUND OF THE INVENTION

1. Field of the Invention

This invention relates generally to the evaluation of the physical properties of samples, and more specifically, to methods employing near-infrared spectrophotometry to simultaneously quantify various physical properties of a multicomponent sample, particularly hydrocarbons.

2. Description of the Prior Art

The need often arises to quantify the physical properties of different gaseous or liquid samples used at various stages of industrial chemical processes. For example, it is frequently required to measure the heats of formation and molecular weights of hydrocarbons being used in petroleum processing and refining.

In the past, the physical properties of samples have typically been measured one property at a time, using testing methods which have been developed to specifically evaluate one particular property. For example, the heat of formation of a particular sample has been determined by actually burning the sample in a calorimeter. Similarly, molecular weight of a sample has been determined by inducing and measuring viscous flow of the sample using a viscometer. In each of these examples, however, the physical test methods measure, or quantify, the physical properties by actually subjecting the sample to the conditions in question. To measure more than one physical property of a particular sample, a plurality of tests must be individually conducted on a plurality of samples. Such an approach to measuring the physical properties of a sample is slow, expensive, and univariate.

More recently, near-infrared spectrophotometric analysis has been used to determine indirectly the qualitative properties of various samples. Such methods are disclosed in Wetzel, D. L. *Anal. Chem* 1983, 55, 1165A to 1176A; Watson, C. A. *Anal. Chem* 1977, 49, 835A–840A, incorporated herein by reference. For example, near-infrared spectrophotometric analysis has been employed to determine the baking quality of flour as shown in Star, S.; Smith, D. B.; Blackman, J. A.; Gill, A. A. *Anal. Proc.* (London) 1983, 20, 72–74; to determine digestibility of forages as shown in Winch, J. E.; Helen, M. *Can. J. Plant Sci.* 1981,, 61, 45; Norris, K. H. Barns, R. F.; Moore, J. E.; Shenk, J. S. *Animal Sci.* 1976, 43, 889–897; and to determine the potencies of pharmaceutical drugs as shown in Rose, J. J. The Pittsburgh Conference, Atlantic City, NJ, March, 1983; paper 707. Each of the above references is incorporated herein by reference.

Use of near-infrared spectrophotometric analysis has many advantages over other methods since it is rapid, relatively inexpensive, and multivariate in that many properties can be tested for simultaneously. To date, however, methods have not been available to use near-infrared spectrophotometric analysis to directly quantify the physical properties of samples, such as the molecular heat and weight of hydrocarbons.

The need existed to develop methods for using near-infrared spectrophotometric analysis to effeciently and inexpensively quantify various physical properties of samples.

SUMMARY OF THE INVENTION

Accordingly, it is an object of the present invention to provide efficient, effective and inexpensive methods for quantifying various physical properties of samples.

It is another object of the invention to provide methods using near-infrared spectrophotometry to quantify a variety of physical properties of different types of samples.

It is another object of the invention to provide methods for quantifying physical properties of multicomponent samples without requiring independent testing to determine the individual components or constituents comprising the sample.

It is another object of the invention to provide such methods which are statistically correlated with calibration data for the specific property and type of sample tested.

It is another object of the invention to provide methods for simultaneously quantifying a plurality of physical properties of a sample using near-infrared spectrophotometry.

It is another object of the invention to provide methods for determining the heat of formation, molecular weight and methyl groups per molecule of hydrocarbon mixtures.

It is another object of the invention to provide methods for quantifying any physical property of a solid, liquid or gaseous sample that is correlated with chemical constituents that respond to near-infrared radiation.

The above, and other objects are achieved by an improved method for quantifying a physical property of a sample. The method comprises an initial step of determining which wavelength or set of wavelengths in the near-infrared spectrum is optimally correlated to the physical property being quantified. Then, weighting, or correcting, constants are calculated for absorbance or reflectance values measured at each of the determined wavelengths. The absorbance or reflectance of the sample at each of the determined wavelengths in the near-infrared spectrum is measured using a spectrophotometer. A reference value for the physical property being quantified is then calculated from the measured absorbance or reflectance of the sample at each determined wavelength, as corrected by the associated weighting constant.

In a preferred embodiment, a statistical algorithm is employed to evaluate a field of test, or calibration, data in order to determine the wavelengths in the near-infrared spectrum which optimally correlate to the physical property to be quantified. Similarly, the statistical algorithm is used to evaluate the field of test, or calibration, data to determine the optimal value of the weighting constants for each of the determined wavelengths. In this manner, the value for the physical property quantified, such as the molecular heat of a hydrocarbon, is most likely to be accurate.

In another embodiment of the invention, a plurality of physical properties of a gaseous or liquid sample can be simultaneously quantified. In its method form, the alternative embodiment of the invention again comprises an initial step of selecting wavelengths, or sets of wavelengths in the near-infrared spectrum which optimally correlate to each of the physical properties to be quantified. For example, a first wavelength, or set of wavelengths, is determined for measuring the molecular heat of a hydrocarbon. Another wavelength, or set of wavelengths, is determined for quantifying molecular weight of hydrocarbons. Similarly, weighting constants corresponding to each of the selected wavelengths are calculated. A spectrophotometer, based on multiple-filter, wavelength-dispersive, or Fourier-transform technology is used to measure the absorbance of the sample at each of the selected wavelengths. Each of the physical properties is then quantified by calculating a reference value from the absorbance measurements of the sample taken from the wavelength or set of wavelengths corresponding to that physical property, the absorbance measurement being corrected by the corresponding weighting constant. In this manner, more than one physical property of a sample can be simultaneously quantified.

In its preferred form, the invention comprises a method for quantifying the molecular heat, or heat of formation, of a hydrocarbon or hydrocarbon mixture. At least two optimal wavelengths are selected in the near-infrared spectrum at which to test the hydrocarbon mixture. The selected wavelengths are in the range of 750 to 2500 nanometers. Weighting constants corresponding to each of the selected wavelengths are determined. The absorbance or reflectance of the hydrocarbon or hydrocarbon mixture at each of the selected wavelengths is measured with a spectrophotometer. The measured absorbance at each selected wavelength is then corrected with the corresponding weighting factor. From the corrected group of absorbance measurements, a reference value corresponding to the molecular heat of the hydrocarbon or hydrocarbon mixture is calculated.

In another preferred embodiment even greater accuracy is achieved by selecting four optimal wavelengths in the near-infrared spectrum at which to measure the absorbance of the sample. A row-reduction algorithm is used to correlate the selected wavelengths with calibration data reflecting the molecular heat values of a pre-tested field of hydrocarbon mixtures. Similarly, a row-reduction algorithm is used to correlate the weighting factors both with the selected wavelengths and with the calibration data reflecting the molecular heat values of a pre-tested field of hydrocarbon mixtures.

BRIEF DESCRIPTION OF THE DRAWINGS

The above and other objects of the invention may best be understood in connection with the following description of the preferred embodiments taken in conjunction with the accompanying drawings, in which.

DESCRIPTION OF THE PREFERRED EMBODIMENT

The present invention provides methods for quantifying various physical properties of samples. The samples tested may be solid, liquid or gaseous. Nearly any physical property may be quantified, as long as the physical property in question is correlated to some compositional or other feature having significant near-infrared absorption or reflectance. It is not necessary to know the actual components or constituents of the sample being tested. In its preferred embodiment, the invention comprises methods and devices employing near-infrared spectrophotometry to evaluate absorbance characteristics to simultaneously quantify the molecular heat, molecular weight, and methyl groups per molecule of hydrocarbon mixtures.

1. The Inventive Methods

The inventive method is used to directly quantify the physical properties of a sample. An initial step in the method is the determination of the wavelength, or set of wavelengths, in the near-infrared spectrum which is optimally correlated to the physical property being quantified. For example, if the molecular heat of hydrocarbons is to be quantified, it is ncessary to first determine the optimal wavelengths in the near-infrared spectrum at which to measure the absorbance or reflectance of the hydrocarbon samples in order to obtain the most accurate results. The wavelengths which are optimal for quantifying the molecular heat of a hydrocarbon may not be the same wavelengths at which absorbance would be measured to most accurately quantify another physical property of a hydrocarbon, such as its molecular weight.

In order to correlate the wavelengths in the near-infrared spectrum with the physical property being quantified, a cross-section of test or calibration samples, which is representative of the actual samples which will be tested, must be fully evaluated. This generally entails measuring and recording the absorbance spectra of each of the calibration samples at a wide range of wavelengths in the near-infrared spectrum. In the test samples, the value of the physical property of interest has already been determined by an alternative technique.

The recorded spectra of the calibration samples are then statistically and mathematically evaluated, to locate the particular wavelength, or set of wavelengths, which optimally represents the physical property being quantified. In its preferred form, a statistical analysis using, for example, the row-reduction algorithm such as that disclosed in Honigs, D. E.; Hieftje, G. M.; Hirschfeld, T. B. *Appl. Spectrosc.* 1983, 37, 491–497, attached hereto as Exhibit A, is used to statistically evaluate the spectra of the calibration samples in order to locate those wavelengths which are best correlated to the physical property being quantified. This article is reproduced in its entirety (except for the abstract and certain figures which have been redacted) as Exhibit A below.

The row-reduction algorithm referred to above is described in full detail in the article attached hereto as Exhibit A.

Briefly, this row-reduction algorithm presents a specific way of solving (by reducing rows of) simultaneous equations such as:

$$2x + 4y = 8$$

$$1x + 8y = 10$$

The algorithm merely codifies the steps so that the solution is found in the same manner every time. Using the above equations as an example, the algorithm would first rewrite the equations so that the largest value comes first:

$$8y + 1x = 10$$

$$4y + 2x = 8$$

Next, each row is normalized by its y coefficient:

$$y + \tfrac{1}{4}x = 10/8$$

$$y + \tfrac{1}{2}x = 2$$

Finally, a subtraction is made (of the first equation from the second) so that the new equations are:

$$y + \tfrac{1}{4}x = 10/8$$

$$0 + \tfrac{3}{8}x = 6/8$$

or:

$$x = 2$$

$$y = 1.$$

The importance of this order of solving the equations increases as more and "noisier" (i.e., more complex to reflect actual, and not theoretical, values) equations are added. By always selecting the largest value, the solution will be least affected by such additional complexity.

With respect to the present invention, for example, if the sample is a hydrocarbon mixture, and the physical property being quantified is the molecular heat of the hydrocarbon mixture, then a representative field of hydrocarbon mixture calibration samples must be fully evaluated to determine which wavelengths in the near-infrared spectrum are optimally suited for quantifying molecular heat. Each calibration sample would be closely controlled and would be carefully prepared with hydrocarbon mixtures which would be representative of the actual samples to be later tested. Alternatively, the calibration samples could be natural and would have the desired physical property determined by an alternative technique. The absorbance spectra of each calibration sample is recorded by a spectrophotometer. The recorded spectra are then statistically analyzed, preferably by computer program, in accordance with the row-reduction algorithm, to determine which wavelengths in the near-infrared spectrum are optimally suited for quantifying molecular heat of any hydrocarbon mixture.

The following example will illustrate how the appropriate wavelengths are selected by the row-reduction algorithm disclosed in Exhibit A. This problem is solved by establishing an equation such as $$(B_1 * W_1) + (B_2 * W_2) + (B_3 * W_3) \ldots = C,$$

where C is the physical property in question, the B values are unknown variables (just like x and y in the previous example), and W is the absorbance or some other spectral response of the sample. This equation is in the same form as the first example and can be solved in the same manner. The only difference is that there is potentially hundreds of wavelengths which might need to be evaluated, and accordingly hundreds of "rows" which might need to be reduced. In practice, equations similar to the above example are created based upon the spectra of many characterized samples. Using the row-reduction algorithm, the largest absorbance value is then selected. This sample will be least affected by noise. The selected sample and wavelength are used to reduce the problem one rank, just as the first row was subtracted from the second one in the previous example. This entire procedure is then repeated with the remaining "rows" until the residuals of the physical or chemical property values are reduced. A simple example is set forth below:

|  |  | Wavelengths |  |  |  |  |  |  |
|---|---|---|---|---|---|---|---|---|
|  |  | a | b | c | d |  |  |  |
| Hydrocarbon | A | 3 | 6 | 2 | 1 | = | 6 | Physical Property |
| Spectra | B | 4 | 3 | 1 | 1 | = | 5 | (e.g., Octane |
|  | C | 2 | 2 | 2 | 3 | = | 11 | Number) |
|  | D | 6 | 4 | 6 | 1 | = | 7 |  |

The value of sample spectrum "D", wavelength "c" is among the largest, and thus is the first wavelength selected by the row-reduction algorithm. This value also is used to solve the first part of the problem, in the manner set forth above, so that additional optimal wavelengths may be determined:

|  | c | a | b | d |  |  |
|---|---|---|---|---|---|---|
| D | 6 | 6 | 4 | 1 | = | 7 |
| A | 2 | 3 | 6 | 1 | = | 6 |
| B | 1 | 1 | 3 | 4 | = | 5 |
| C | 2 | 2 | 2 | 3 | = | 11 |

Thereafter, the data is reduced as described above:

|  | c | a | b | d |  |  |
|---|---|---|---|---|---|---|
| D | 1 | 1 | 2/3 | 1/6 | = | 7/6 |
| A | 0 | 1/2 | 7/3 | 1/3 | = | 11/6 |
| B | 0 | 3 | 7/3 | 5/6 | = | 23/6 |
| C | 0 | 0 | 1/3 | 4/3 | = | 13/3 |

The next wavelength choice is sample spectrum "B", wavelength "a", because it is the largest residual. This procedure is continued until the residual values in the physical property column become insignificant, and all of the equations essentially are solved. Again, this row-reduction algorithm is only one of many possible methods to perform such a statistical analysis.

Once the optimal wavelengths at which to evaluate the actual samples are selected, weighting or correction constants must be determined. The weighting constants are used to statistically correct the actual absorbance measurements which are taken at the selected wavelengths in order to quantify the physical properties. The row-reduction algorithm techniques disclosed in Honigs, D. E.; Hieftje, G. M.; Hirschfeld, T. B. *Appl. Spectrosc.* 1983, 37, 491–497 may again be used to statistically evaluate the pre-tested calibration samples in order to determine the values of the weighting constants which, when used to correct the actual absorbance measurements at the previously selected wavelengths, result in an acceptably accurate reference value for the physical property being quantified. Specifically, such weighting (or correction) constants are represented by the solutions to the equations which have been solved in the manner illustrated above (e.g., the previously unknown x and y values).

Having determined the optimal wavelengths at which to make absorbance measurements and the corresponding weighting constants in order to most accurately quantify the physical property of the sample being evaluated, the following relation results:

$$Ref = (WC(a) \times ABS(a)) + (WC(a+1) \times ABS(a+1)) + \ldots + (WC(b) \times ABS(b)) \quad (1)$$

where Ref is the reference value of the physical property being quantified, WC(a) is a weighting constant determined by the statistical analysis to best correlate to a selected wavelength, ABS(a) is the measured absorbance of the sample at the same selected wavelength, and b is the number of wavelengths determined by the statistical analysis to best quantify the particular physical property of the sample. Equation (1) can be rewritten follows:

$$\text{Ref} = \sum_{a=1}^{b} WC(a) \times ABS(a) \quad (2)$$

A spectrophotometer is used to record the absorbance spectra of an actual sample for which the physical property in question is being quantified. The absorbance values of the sample at each of the wavelengths previously determined to best correlate with the data from the calibration samples are then inserted in equation (1) or (2), corrected by the corresponding weighting constants, and added together to result in a numerical reference value representing the quantity of the desired physical property.

In sum, a basic embodiment of the invention is a method for quantifying a physical property of a sample comprising the steps of (a) using a statistical algorithm to determine which wavelengths in the near-infrared spectrum optimally correlate to the particular physical property being quantified; (b) using a statistical algorithm to determine numerical weighting constants which are optimally correlated to the determined wavelengths; (c) measuring with a spectrophotometer the absorbance of a sample at each of the determined wavelengths; and (d) calculating according to equation (1) or (2) a reference value for the physical property of the sample.

Another embodiment of the invention comprises a method for simultaneously quantifying a plurality of physical properties of a sample. In this embodiment, the row-reduction algorithm is employed to evaluate a representative field of calibration samples to determine which wavelengths, or different sets of wavelengths, are optimally correlated to each of the physical properties being quantified. Thus, for example, if three physical properties of a sample are to be simultaneously quantified, there may be three different wavelengths, or sets of wavelengths, in the near-infrared spectrum at which absorbance measurements will be taken in order to optimally quantify each physical property. The row-reduction algorithm is also used to evaluate the field of calibration samples to determine the values for weighting constants which optimally correlate to each of the selected wavelengths in order to obtain statistically acceptable or valid results.

Having determined the wavelengths, or sets of wavelengths for each physical property at which to measure absorbance of the sample and the corresponding weighting constants, the following relationships are used to quantify the physical properties:

$$\text{Ref}(1) = \sum_{a=1}^{b} WC(1)(a) \times ABS(1)(a) \quad (3)$$

$$\text{Ref}(2) = \sum_{a=1}^{c} WC(2)(a) \times ABS(2)(a) \quad (4)$$

-continued $$\text{Ref}(n) = \sum_{a=1}^{d} WC(n)(a) \times ABS(n)(a) \quad (5)$$

where: Ref(1), Ref(2) and Ref(n) each represent reference values for different physical properties being quantified; n is the number of physical properties being quantified; WC(1), WC(2) and WC(n) each represent the weighting constants determined to correlate to the wavelengths, or sets of wavelengths used to quantify the associated physical property; b, c and d represent the number of selected wavelengths within the sets determined to optimally correlate to a particular physical property; and ABS(1), ABS(2) and ABS(n) represent the measured absorbance of the sample at each selected wavelength, or set of wavelengths, correlated to particular physical properties. Equations (3), (4) and (5) can be simplified as follows:

$$\text{Ref}(m)_1{}^n = \sum_{a=1}^{b} WC(m)(a) \times ABS(m)(a) \quad (6)$$

A spectrophotometer is used to measure and record the absorbance spectra of the actual sample for which the plurality of physical properties are being quantified. The absorbance values of the sample at each of the selected wavelengths, or set of wavelengths, corresponding to a first physical property are then inserted in equation (6), corrected by the corresponding weighting constants, and added together to result in a numerical reference value representing the quantity of the first physical property. The procedure is repeated for each of the physical properties being quantified.

Thus, a second basic embodiment of the invention is a method for quantifying a plurality of physical properties comprising the steps of: (a) using a statistical algorithm, such as the row-reduction algorithm, to select sets of wavelengths in the near-infrared spectrum which optimally correlate to each of the physical properties being quantified; (b) using a statistical algorithm, such as the row-reduction algorithm, to determine a weighting factor corresponding to each of the selected wavelengths; (c) measuring with a spectrophotometer the absorbance of the sample at each of the selected wavelengths; and (d) calculating for each physical property being quantified a reference value, the reference value depending upon the measured absorbance of the actual sample at each wavelength within the corresponding correlated set of wavelengths, the measured absorbance at each wavelength being corrected by the corresponding weighting constant.

EXAMPLE

The methods and devices of the present invention were used to simultaneously quantify the molecular heat, molecular weight and the number of methyl groups per molecule in a variety of hydrocarbon mixtures. Calibrations accurate to 1.2 kcal/mole for determining heats of formation, 1.5 g/mole for determining mean molecular weight, and 0.057 groups/molecule for determining methyl groups per molecule were obtained.

1. The Calibration Samples

Hydrocarbon mixtures were synthetically prepared by weighing aliquots of reagent-grade benzene (Mallinckrodt) and cyclohexane (MC&B), and spectroanalyzed iso-octane and n-heptane (Fisher) into gas-tight vials. Ninety of the hydrocarbon mixtures, ranging from 0% to 100% concentration of each hydrocarbon, were prepared as calibration samples for this example. The error in each standard concentration was approximately 0.05%, estimated by propagation of an error in weighing of 0.01 g.

The absorbance spectra of each of the calibration samples was recorded by a Digilab FTS-15C Fourier-transform spectrophotometer equipped with a Si beam splitter, a PbSe detector operated at 300° K., and a $CaF_2$ flow-through cell. The instrumental resolution was nominally 4 $cm^{-1}$ and boxcar apodization was employed. Throughout the data collection, the calibration cell holding the hydrocarbon mixture was fixed in position in order to minimize any pathlength errors.

The correlation between a desired physical property and the near-infrared spectrum was generated by the row-reduction algorithm disclosed in Honigs, D. E.; Freelin, J. M.; Hieftje, G. M.; Hirschfeld, T. B. *Appl. Spectrosc.* 1983, 37, 491–497 set forth below as Exhibit a. Briefly, the row-reduction algorithm is used to statistically evaluate the spectrum of each sample at a large number of wavelength combinations until a particular combinations reached which quantifies the desired physical property within an acceptable degree of error. Each correlation was developed by dividing the 90 samples into calibration sets of 42 samples and performance-verification sets of 48 samples.

Since in this example there are four chemical components or constituents which sum to 100 percent of the sample and since three of the components can vary independently, three wavelengths are enough to quantify the physical properties of the hydrocarbon samples. However, one additional wavelength is necessary to account for instrumental errors.

Initially, the calibration sets were evaluated for the best four analytical wavelengths in the range of 750–2500 nm. 2000 wavelengths within this range were searched. This initial evaluation of the calibration test samples provided adequate results for quantifying molecular weight and heats of formation, but unsatisfactory results for the determination of methyl groups per molecule. It was determined empirically that increasing the number of analytical wavelengths to six resulted in an improved calibration for quantifying methyl groups per molecule.

The physical properties of the performance verification samples were then quantified in accordance with equation (6) above. Reference values for heat of formation, mean molecular weight, and methyl groups per molecule were obtained by multiplying the absorbance value at the correlated wavelengths of each hydrocarbon verification sample by the associated weighting constant, and then adding the contributions from each component. The reference values can be compared to the true heats of formations and molecular weights of each of the pure hydrocarbons obtained from Neast, R. C., Astle, M. J., Eds. "CRC Handbood of Chemistry and Physics", 60th Edition, CRC Press; Boca Ratan, Fl 1979, incorporated herein by reference. By propagation-of-error calculations the error of the reference values was approximately 0.1%.

2. Results

Figure 1:
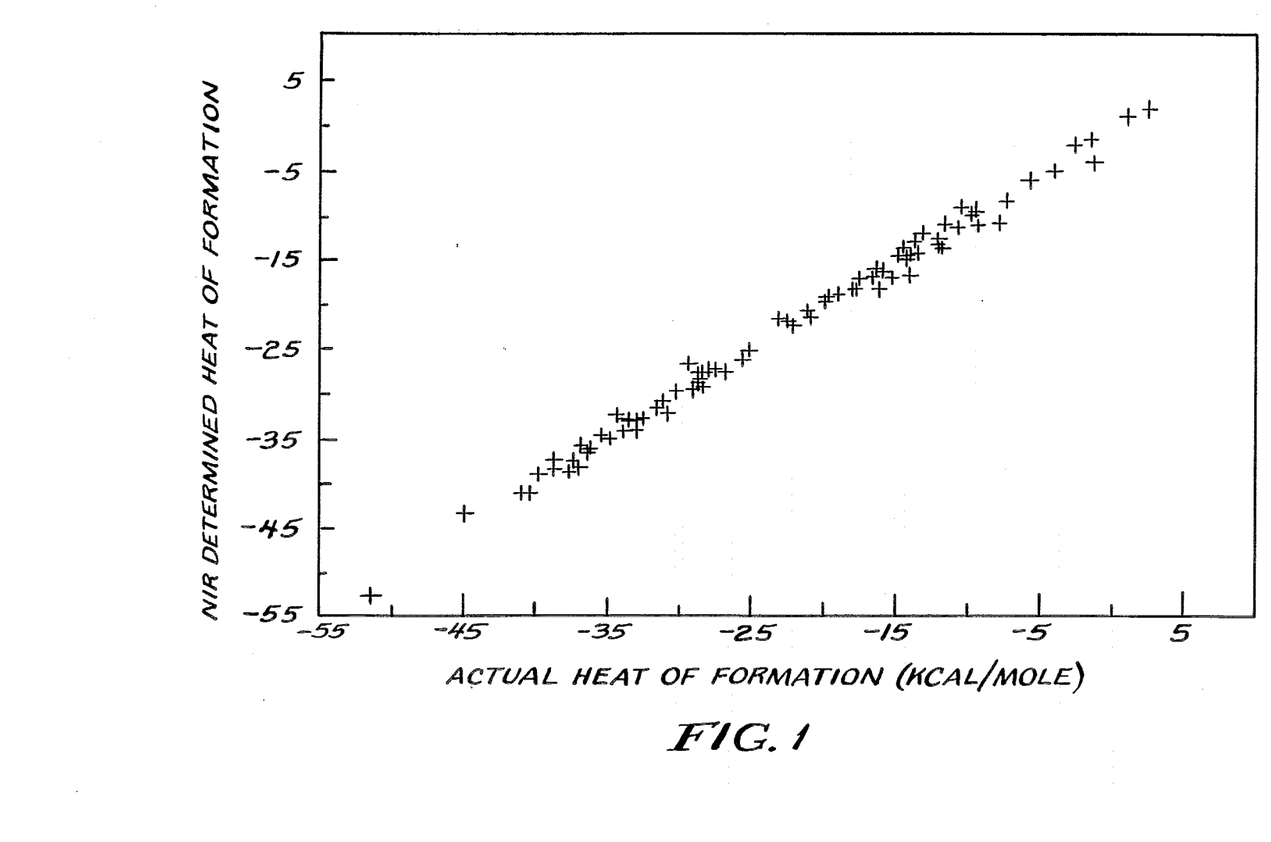
FIG. 1 is a graph of the heat of formation of a series of hydrocarbon mixtures as determined by the methods of the present invention.
Figure 2:
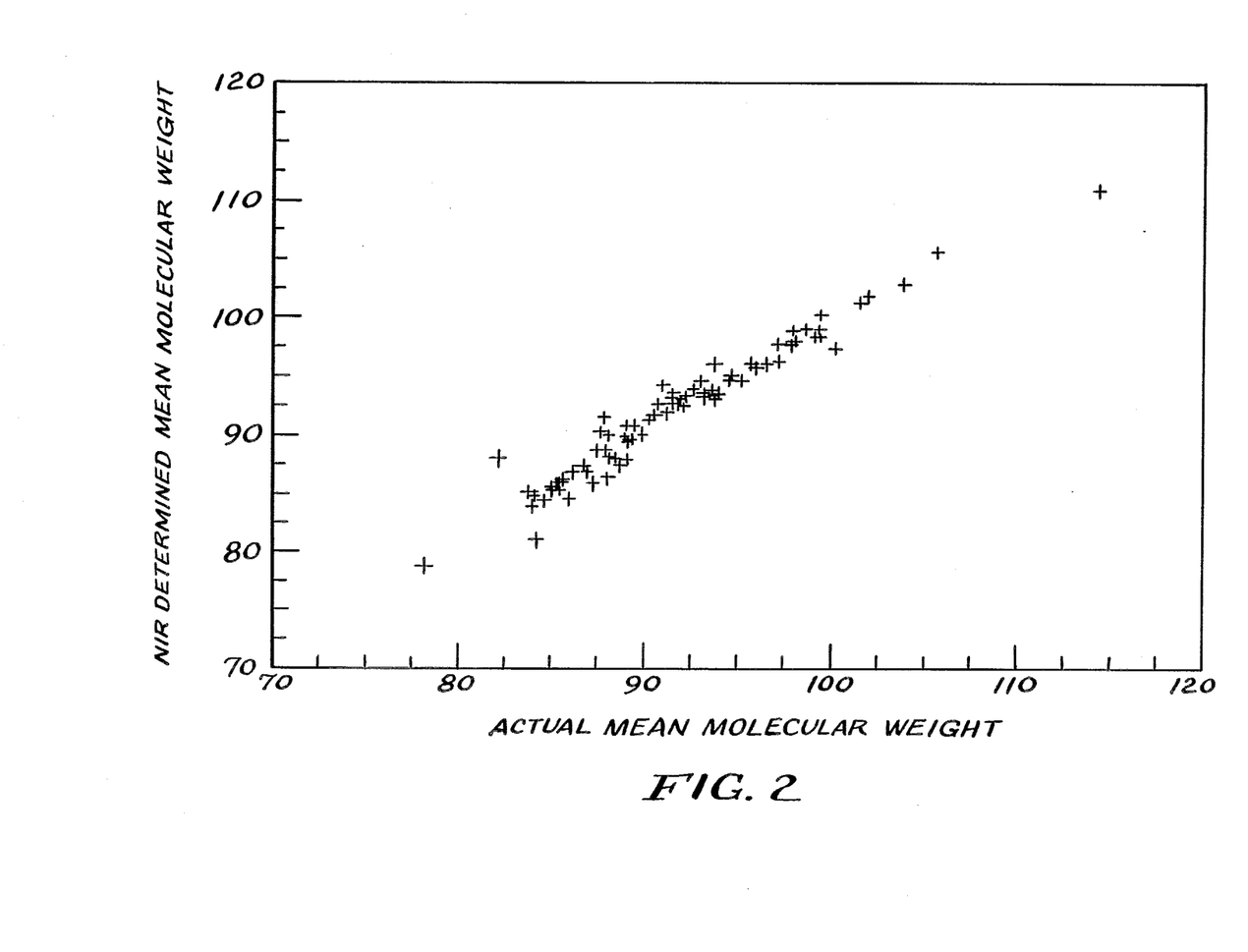
FIG. 2 is a graph of the molecular weight of a series of hydrocarbon mixtures as determined by the methods of the present invention.
Figure 3:
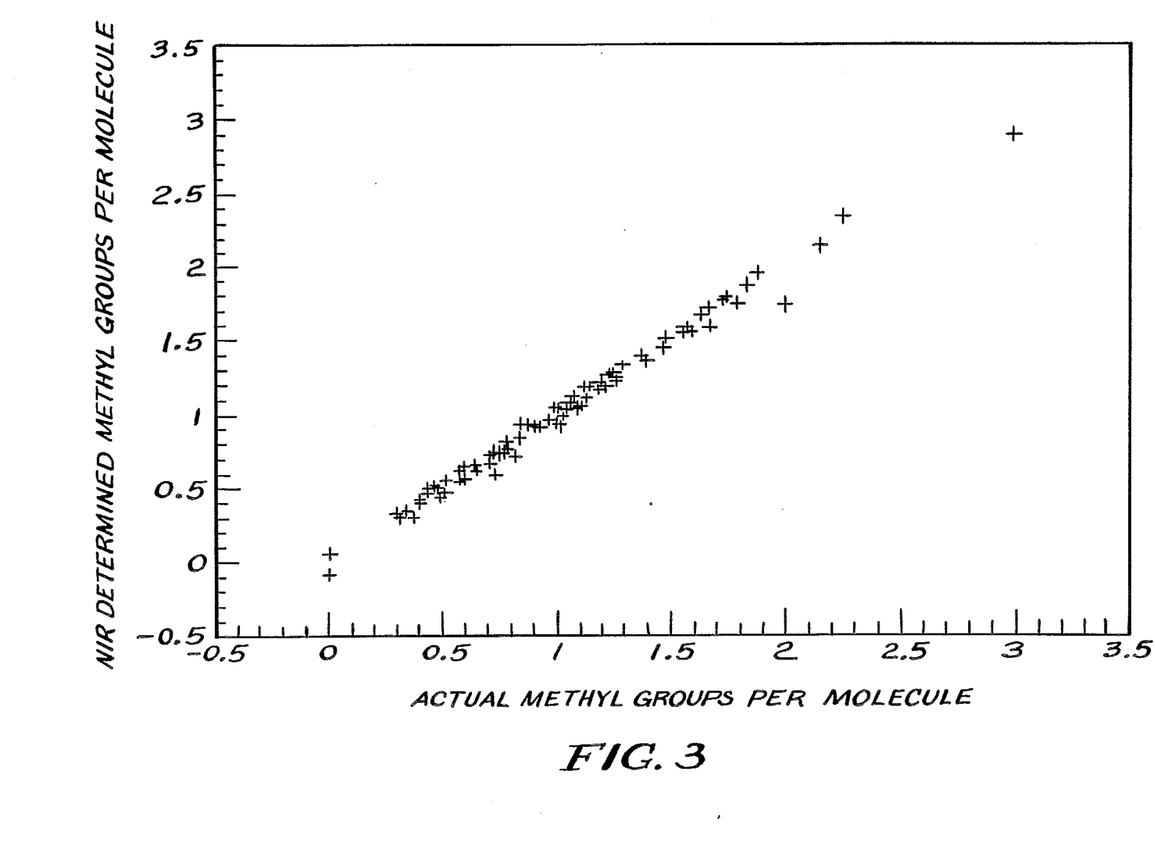
FIG. 3 is a graph of the methyl groups per molecule for a series of hydrocarbon mixtures as determined by the methods of the present invention.

The results of the spectrophotometric quantifications for heat of formation, mean molecular weight, and the number of methyl groups per mole are shown in FIGS. 1 through 3. Correlated analytical wavelengths and weighting factors for the calibration samples are listed in Table I below.

TABLE I

Wavelengths and Weighting Coefficients used to Spectrophotometrically Determine Heat of Formation, Mean Molecular Weight, and Methyl Groups per Mole in a Series of Hydrocarbon Mixtures.

| Heat of Formation | | Mean Molecular Weight | | Methyl Groups/Molecule | |
|---|---|---|---|---|---|
| Wavelength, nm | Weighting Factors | Wavelength, nm | Weighting Factor | Wavelength, nm | Weighting Factors |
| 2181 | −3.8 | 2472 | 6.2 | 2346 | −0.012 |
| 2150 | 9.4 | 2440 | 14.5 | 2323 | −0.104 |
| 1958 | −2.7 | 2319 | −2.7 | 2319 | 0.097 |
| 1701 | −2.9 | 1352 | −10.8 | 2305 | 0.034 |
| | | | | 1753 | −0.023 |
| | | | | 1671 | 0.002 |

The coefficients for mean molecular weight listed in Table 1 above determine the mean number of micrograms per molecule in the sample. The mean molecular weight is determined by dividing 1000 by the calculated number of micrograms/gram. The verification statistics are summarized in Table II, below.

TABLE II

Calibration results for the Spectrophotometric Determination of Heat of Formation, Mean Molecular Weight, and Methyl Groups per Molecule in a Series of Hydrocarbon Mixtures.

| Calibrated Property | Standard Error of Calibration | Standard Error of Performance | Range of Samples Analyzed |
|---|---|---|---|
| Heat of Formation including pure benzene | 0.8 kcal/mole | 2.0 kcal/mole | −51.5 to 19.8 kcal/mole |
| Heat of Formation excluding pure benzene | 0.8 kcal/mole | 1.2 kcal/mole | −51.5 to 2.3 kcal/mole |
| Mean Molecular weight | 1.1 g/mole | 1.5 g/mole | 78 to 114 g/mole |
| Methyl Groups per Molecule | 0.053 groups molecule | 0.057 groups molecule | 0 to 3 groups molecule |

From Table I one can quantify the physical property of a hydrocarbon sample in a manner analogus to that illustrated in Eq 7:

$$\begin{aligned}\text{Heat of} \\ \text{Formation}\end{aligned} = -3.3 \times Abs(2181) + 9.4 \times Abs(2150) \\ -2.7 \times Abs(1958) + 2.9 \times Abs(1701) \quad (7)$$

where Abs(x) is the sample absorbance at x nm. Similar equations derive from Table I for determining mean molecular weight and methyl groups per molecule.

For the determination of the heats of formation of the hydrocarbon mixtures there are two results reported in Table II, one including and one excluding pure benzene. This comparison was made because the calibration sample with the largest heat of formation (0.95 Kcal/mole) was considerably below the heat of formation of pure benzene (19.82 Kcal/mole). For the other physical properties the disparity between the calibration samples and benzene was much smaller and the calibration was therefore more reliable.

FIGS. 1–3 and Table II indicate clearly that the inventive methods and devices can be used to accurately quantify the physical properties of samples.

3. Discussion

It is noted that different wavelengths, or sets of wavelengths, were chosen to determine each of the different physical properties. However, any one of these wavelength sets could, if desired, be used to determine all of the physical properties and chemical-constituent concentrations. However, because the different physical properties place different emphasis on the four components of the sample, the error of each must be weighted differently in the overall optimization. This is better done by selecting a different set of optimal analytical wavelengths for each physical property being quantified.

In the case of the determination of methyl groups per molecule the optimal wavelengths determined by the row-reduction algorithm include a pair that are closely spaced (2323 and 2319 nm) with equal but opposite multipliers: essentially a derivative. This type of measurement is particularly efficient for small-peak-shift resolution, as is found often in the severely overlapped carbon-hydrogen (C-H) stretch bands. The use of a derivative as an adaptive response by the row-reduction algorithm solves the measurement problem but increases the number of wavelengths required.

In addition to identifying the chemical nature of many samples, a near-infrared spectrum contains quantitative information about the sample constituents. Since it is possible with the inventive methods to quantify the chemical constituents, it is also possible to determine any physical property that has a first-order dependence on their concentration. The heat of formation or mean molecular weight of a sample, for example, could be independently determined by a near-infrared method calibrated for the concentration of each of the sample constituents and by then substituting those concentration values into the proper equation. The multiple-linear-regression mathematics employed by the inventive methods make a separate substitution step unnecessary; the invention deduces automatically the exact relationship between the sample constituents and the physical property of interest. This feature makes near-infrared spectrophotometry extremely useful not only for quantifying physical properties, but also for evaluating physical properties which are related to the chemical constituents in an unknown manner, such as the "baking quality" of flour.

If the present invention is used to measure the near-infrared spectrum of a sample by diffuse reflectance, it is also possible to determine additional information about the physical properties of that sample. For example, changes in macroscopic texture and microscopic crystal structure will change the albedo of the sample. This type of information allows near-infrared reflectance methods to locate material defects and determine the "hardness" of a sample.

In general, any sample property that is a second-order of higher function of concentration cannot be directly determined by the above-disclosed embodiments of the inventive methods and devices since the correlation step employs only first-order mathematics. The exceptions to this rule are properties which have a first-order relationship to a spectrum, even if this relationship to concentration is different, such as that in hydrogen bonding. Second-order functions can be accommodated in the present invention by using a series of linear approximations or higher-order regression mathematics. The present invention is thus able to determine any physical property that is correlated with those chemical constituents that respond to near-infrared radiation, as long as the property in question is correlated to some compositional or other feature having a significant near-infrared absorption.

While the above example describes certain methods of the present invention, they are not to be construed as limitations. For example, the methods described above may employ the evaluation of reflectance characteristics as well as absorption characteristics. Further, if the precise wavelengths as which to quantify the physical property of the sample are known, a fixed wavelength photometer can be employed, instead of the more complex spectrophotometers, to measure the absorbance or reflectance of the sample. In addition, the inventive methods may be employed outside the near-infrared region if appropriate for the types of samples being examined. Thus, as one skilled in the art would recognize, many modifications may be made in the methods of the present invention without departing from its spirit or scope.

EXHIBIT A

[Title and Abstract Redacted]

INTRODUCTION

A. Overview. The application of near-infrared reflectance analysis (NIRA) as an analytical technique has been concentrated mainly in the agricultural area where it originated.[1-4] These agricultural applications are characterized by the need to determine a limited number of constituents in a very large number of individual but similar samples. In contrast to this situation, samples encountered in most industrial analytical laboratories are widely varied in kind and the number of very similar samples is limited.

If NIRA is to be applied broadly to industrial chemical analysis, it must be modified to reduce sharply the developmental effort needed to set up an individual method. At present, the establishment of a NIRA procedure requires the assembly of a fairly large set of standard samples where composition has already been established by a reference method or methods. The reflectance of the samples must then be measured at a substantial number of points in the near infrared spectral region, and the resulting data subjected to a multilinear regression algorithm. This algorithm then generates the choice of analytical wavelengths and yields a "correlation equation" which relates concentration of desired constitutents to reflectance at various near-infrared wavelengths. This latter calculation step is very demanding of computer hardware and processing time, particularly for high-performance NIRA instruments that cover a wide range of wavelengths, a probable requirement for industrial analysis. In fact, these computational requirements are so demanding that they have often forced shortcuts in methods development and optimization and have limited the performance of the NIRA system. This limitation is manifested by incomplete optimization of the analytical wavelength set, whereby either too few wavelengths are examined, abridged wavelength selection criteria are used, or too few or incorrect wavelengths are selected for the NIRA procedure.

This limitation also encourages incomplete testing and evaluation of the developed NIRA method, which leads to the widespread use of poorly understood algorithms and the retarded development of improved ones. This lack of understanding and the workload of existing methods have often been great enough to discourage people from examining the NIRA approach and have acted as a brake on its wider acceptance and application.

In the present paper, an algorithm is described and evaluated for substantially accelerating the wavelength and calibration coefficient selection process of NIRA. This algorithm is used to find "correlation equations" for protein in wheat and benzene in a hydrocarbon mixture. Bias-corrected standard errors of prediction obtained with the new algorithm reached 0.26% protein in wheat and 1.01% benzene by volume. Comparisons of the algorithm with several others based on regression show improvements in computation time ranging from a few percent to as much as 200-fold. Also discussed is how the novel method might prove advantageous in the reduction of overfitting and in the improvement of NIRA accuracy.

B. Calibration Procedures in NIRA. The general pattern for establishing a NIRA calibration is described in a review article by Watson,[5] and will be briefly summarized here for clarity. The first step in establishing a NIRA calibration is to obtain a sample set in which the desired characteristic or sample constituent has been previously determined by a reference chemical or spectroscopic technique. An example of such a set would be wheat samples whose protein content had been established by Kjeldahl determinations. The sample set is randomly divided into two subsets, one for solving the regression procedure (training) and one for testing the regression (prediction). Next, the near-infrared diffuse-reflectance spectrum for each sample is obtained. The spectra from the training set are then analyzed by some form of multiple linear regression. Typically, $-\log$ reflectance values (R) are regressed against the chemically determined concentrations to identify a group of wavelengths at which R best predicts the desired constituent in the training set. A number of alternative linear regression techniques are currently available to establish the NIRA calibration. These techniques include (but are not limited to) stepwise, all possible combinations, all possible pairs stepwise, and all possible triplets stepwise.

Stepwise regression is well known in statistical applications.[6] In its most general form a stepwise regression algorithm calculates the linear regression between two sets of variables and establishes a statistical confidence level to their degree of coherence. It then adds new values to or deletes old ones from one of the sets in an attempt to improve the coherence; coherence is usually expressed in terms of a correlation coefficient. Procedures involving the addition or deletion of values are called forward stepwise and backward stepwise regression, respectively. In its application to NIRA, forward stepwise regression involves the addition of R values at new wavelengths and suffers from the problem that the newly added wavelength is often not the best wavelength to add. Moreover, background interferences can cause omission of an important wavelength. Backward stepwise regression in NIRA requires that the total number of wavelengths that are employed be small enough that the regression containing all wavelengths can be calculated in a reasonable time, as the starting point for the backwards stepping. This requirement is usually inconsistent with the amount of data generated by a spectral scanning instrument.

The "all-possible-combinations" regression[6] improves upon the forward stepwise approach, in that background interferences do not bias the selection of wavelengths. The drawback to the all-possible-combinations technique is the enormous number of calculations it requires. This number is equal to $2^m$, where $m$ is the total number of wavelengths being employed, restricting this approach to those applications with the smallest data sets.

In an effort to combine the advantages of the stepwise and all-possible-combinations methods, several hybrid techniques such as "all-possible-pairs stepwise" and "all-possible-triplets stepwise" have been developed.[7] These techniques begin with all possible pairs or triplets of wavelengths, respectively, and proceed by means of a forward stepwise regression. In this way, the best pair or triplet of wavelengths cannot be hidden by background interferences, yet the number of required calculations is much less than in the all-possible-combinations method. To ensure self-consistency, one of the wavelengths earlier adopted in the calibration is dropped and the best wavelength to add is then determined by stepwise regression. If the calibration is self-consistent, this new wavelength is the same as the one just deleted. If not, the new wavelength is retained, a different one deleted, and the process repeated until the wavelength which is deleted is subsequently restored by the regression process.

After using any of these regression techniques one obtains a calibration of the form:

$$C = B_0 + B_1 R_1 + B_2 R_2 + \ldots + B_j R_j \quad (1)$$

where $B_0 \ldots B_j$ are the cofficients of intercept and partial slopes from the regression equation, $R_j$, is $-\log$ (reflectance) of the sample at the $j$th wavelength, and $C$ is the concentration of the desired species in the sample.

Once the $B_o$ through $B_j$ coefficients are determined, the standard deviation between the actual and predicted concentrations for the training set (corrected for the statistical degrees of freedom) is computed and called the "standard error of estimation" (SEE). The mathematical definition of SEE is given in Eq. (2).

$$SEE = \left[ (N_s - 1 - N_u)^{-1} \sum_{i=1}^{N_s} e_1^2 \right]^{\frac{1}{2}} \quad (2)$$

where $N_s$ is the number of samples in the training set, $N_u$ is the number of wavelengths kept, and $e_i$ is the difference between the true component concentration and the value predicted by Eq. (1) for the $i$th sample.

Next, the deduced regression equation [Eq. (1)] is used to calculate the concentration of the desired constituent in each of the samples in the prediction set. From these computed concentrations and those known from the earlier independent chemical analysis (e.g., Kjeldahl determination), another standard deviation is determined, termed the "standard error of prediction" (SEP). The definition of SEP is given in Eq. (3).

$$SEP = \left[ (N_s' - 1)^{-1} \sum_{i=1}^{N_s'} e_1^2 \right]^{\frac{1}{2}} \quad (3)$$

where $N_s'$ is the number of samples in the prediction set.

The value of SEP is typically used as a measure of the performance of Eq. (1); however, a bias-corrected SEP better estimates how well the calibration will perform in the field, where routine comparisons between NIRA results and results from the reference chemical method are periodically used to adjust the long-term drift of the NIRA spectophotometer. This bias-corrected SEP is given by the equation:

$$SEP \text{ (biased)} = \left[ (N_s' - 1)^{-1} \sum_{i=1}^{N_s'} (e_1 - \text{Bias})^2 \right]^{\frac{1}{2}} \quad (4)$$

where $$\text{Bias} = (N_s')^{-1} \sum_{i=1}^{N_s'} e_1 \quad (5)$$

C. Row-reduction. Because NIRA is similar to multicomponent UV-visible spectrophotometry, it would be very useful to transfer the knowledge and technology of this latter field to NIRA. Unfortunately, this transfer is not straightforward. A NIRA spectrum contains virtually no peaks attributable to a single species, so individual "absorptivities" cannot be measured and background corrections are very complex. In fact, it was this very complexity that led to the introduction of regression techniques. Unfortunately, multilinear regression techniques are very easily overfitted and can be very slow.

In an attempt to reduce the overfitting of multilinear regression and shorten computation time, a simplifying assumption has been made in the present study. Specifically, if the errors in the reference chemical method and in the measured diffuse reflectance spectrum are small, a simple linear-algebra solution of $j$ unknowns with $j$ equations will give a good first approximation to a multilinear regression. To test the assumption, the Gauss-Jordan reduction[8] method for treating linear equations was used to solve Eq. (1) for several NIRA sample sets. The authors have elected to call this particular application of Gauss-Jordan reduction "row-reduction."

I. THEORY

Gauss-Jordan reduction is a general approach to solving a system of $n$ equations for $n$ unknowns. A full description of the mathematics involved can be found in Ref. 8. Briefly, to solve for a single variable in a system of equations such as the one shown in Eq. (6) [which can be rewritten in matrix form as Eq. (7)], each equation can be multiplied by some constant and then subtracted from another equation. For example, to solve Eqs. (6) and (7) for the variable $x$, the second row can be multiplied by $-\frac{1}{2}$ and the third row multiplied by $-3/2$. These operations transform Eq. (7) into Eq. (8).

$$\begin{aligned} 3x + 2y + 3z &= 16 \\ 6x + 2y + 8z &= 28 \\ 2x + 6y + 4z &= 26 \end{aligned} \quad (6)$$

$$\begin{bmatrix} 3 & 2 & 3 & 16 \\ 6 & 2 & 8 & 28 \\ 2 & 6 & 4 & 26 \end{bmatrix} \quad (7)$$

$$\begin{bmatrix} 3 & 2 & 3 & 16 \\ -3 & -1 & -4 & -14 \\ -3 & -9 & -6 & -39 \end{bmatrix} \quad (8)$$

When row 1 of Eq. (8) is added to rows 2 and 3, the resulting matrix is shown in Eq. (9).

$$\begin{bmatrix} 3 & 2 & 3 & 16 \\ 0 & 1 & -1 & 2 \\ 0 & -7 & -3 & -23 \end{bmatrix} \quad (9)$$

This process can be continued to solve for $y$ and $z$. When the matrix is entirely solved, it is in the form shown in Eq. (10)

$$\begin{bmatrix} I & \begin{vmatrix} A_1 \\ A_2 \\ \cdot \\ \cdot \\ \cdot \\ A_p \end{vmatrix} \end{bmatrix} \quad (10)$$

where I is the identity matrix and $A_p$ is the answer to the pth variable in the equation. For Eq. (6), $x$ is the first variable, $y$ is the second, and $z$ is the third, and their solutions are found in $A_1$, $A_2$, and $A_3$, respectively.

The adaptation of Gauss-Jordan reduction to row-reduction NIRA is straightforward. The calibration of a NIRA sample set proceeds through the collection of spectra as described earlier. After the diffuse reflectance spectrum of each sample is obtained, the first $j$ [where $j$ is the number of terms in Eq. (1)] reflectance (R) values in the spectrum for each sample in the training set are placed in a matrix. It is important to recognize that the $j$ reflectance values used in this matrix do not constitute the *entire* sample spectrum. Rather, they are merely the first $j$ values of the entire spectrum. The standard concentration of the sought-for species in each sample of the training set is also placed in the matrix; these concentrations correspond to the known values (right-hand side) of Eq. (6) and are termed the augmented portion of the matrix. The resulting matrix is shown pictorially in FIG. 1 which is just the matrix form of the set of equations [like Eq. (1)] resulting from several samples. The unknowns on the left-hand side of the matrix illustrated in FIG. 1 correspond to the $B_1$ through $B_j$ values of Eq. (1).

To solve the matrix in FIG. 1 via Gauss-Jordan reduction, the matrix rows are rearranged to cause the largest reflectance (R) value in each column to lie on the diagonal. This rearrangement is called row interchanging. The matrix in FIG. 1 is then solved successively for each $B_n$ term as described earlier; as a consequence, the remaining R values become orthogonal to those which were used to solve for the B terms. This behavior can be seen in Eq. (9); the first row of Eq. (9) is the only one which contains information about the unknown value $x$. When the matrix is completely solved and reduced to the form of Eq. (10), the first row is orthogonal to the rest of the matrix and contains information only about $x$. By means of row interchanging, the most mutually orthogonal samples are chosen to determine the $B_n$ terms.

After the $B_n$ values have been found, the solution is validated by comparing actual vs predicted values for the training set and calculating a SEE and a correlation coefficient (r value). This r value is saved for comparison with later solutions.

Once the r value for the first matrix has been computed, the column corresponding to the wavelength with the *largest* B multiplier is dropped from the matrix and the R values for the next $(j+1)$ wavelength are put in its place. The computation and matrix solution are then repeated. After every wavelength that was recorded in the original spectrum has proceeded through this computation, the entire process is repeated, using the final matrix as a starting point. All wavelengths are again stepped through the matrix solution procedure; after this second iteration, the combination which gave the best r value is recalled and used as the solution to Eq. (1).

In the wavelength-stepping procedure, the dropping of the column with the *largest* B value has an interesting effect. If reflectances at all wavelengths have roughly equivalent magnitudes, a reasonable assumption in the

[Fig. 1 redacted]

near infrared, the wavelength with the largest B value will contain the most information about the sought-for species. Because it is this "most important" wavelength that is dropped, the selection operation rapidly collects the most orthogonal wavelengths (those least correlated with the desired constituent and most correlated with background). This same selection criterion prevents the matrix from becoming "ill determined" and therefore subject to large roundoff error. An ill determined matrix typically contains very large positive and negative B values in pairs. Because the largest positive B value will be dropped by the selection criterion of row reduction, the ill-determined pairs are broken up and the matrix becomes well behaved and less subject to roundoff error.

When the procedure steps through the wavelengths a second time, the same selection criterion naturally seeks out the wavelength best correlated with the desired constituent. As each new wavelength is added, the solution to the linear equation uses all of the collected background wavelengths to calculate a background-corrected calibration. Because the best correlation with the concentration of the desired constituent is stored, the wavelength which is retained is the one that shows the greatest ability to be background-corrected.

One might initially surmise that it would be better to drop the smallest rather than the largest B value during the wavelength-stepping procedure. However, because bands in the near-infrared portion of the spectrum are strongly overlapped, precise background correction is critical for a successful calibration. Dropping the smallest B value during the row-reduction process would keep only those wavelengths which are most highly correlated with the desired constituent and would fail to provide adequate background correction.

II. EXPERIMENTAL

A set of simulated spectra was used initially to test the row-reduction algorithm. Four series of random numbers were used to simulate the absorbance spectrum of four pseudo-species at 15 pseudo-wavelengths in each spectrum. Ten pseudo-samples were generated by combining randomly selected amounts of each of the four pseudo-species. The spectrum of each sample was then calculated from a strict application of Beer's law, assuming additivity of the absorbances of the sample constituents. After the simulated spectra were computed, various levels of random noise were added to the spectral and concentration values.

In the first real test of the new algorithm, a set of absorbance data for methyl red and methyl orange mixtures, obtained from Ref. 9, was used to predict solution pH. The data consisted of absorbances obtained at discrete wavelengths ranging from 375 to 575 nm.

In order to compare the new algorithm with those employed earlier, a set of 100 near-infrared diffuse-reflectance spectra of ground wheat samples was obtained from the USDA, Beltsville, MD, and used to predict the percent protein in wheat. Each sample had been assayed for protein by 32 replicate Kjeldahl determinations. The exact description of the data set has been published elsewhere.[10] The data were used as received with the exception that only every fourth wavelength was considered, for total of 125 wavelengths. These 125 wavelengths ranged from 1 to 2.6 $\mu$m in increments of 12.8 nm. The reported instrumental bandpass was 7 nm and no spectral averaging was used. Fifty samples were used to train the new algorithm and the remaining 50 were used to test it.

Finally, a set of 94 absorbance spectra of synthetic mixtures of benzene, cyclohexane, n-heptane, and isooctane was used to predict the concentrations of benzene. These spectra were obtained from a Digilab FTS 15C Fourier-transform infrared spectrometer at a resolution of 8 $cm^{-1}$. A spectral range of 1.67 to 2.5 $\mu$m was considered. Of the 94 measured spectra, 47 samples were used to train the algorithm and 45 samples were used to test it. Two sample spectra were discarded because of verified instrumental error during their acquisition.

III. RESULTS

A. Simulated Spectra. Experiments with simulated spectra simplified the evaluation of the row-reduction algorithm under varying conditions. Several general trends were apparent from these experiments: (1) when no noise was added to the simulated spectra, the algorithm generated an exact solution to Eq. (1) with a SEE of 0; (2) when noise was selectively added, the algorithm consistently chose those wavelengths with the least noise; (3) when additional simulated wavelengths were added but which contained no information (i.e., were not related to sample composition), they were never chosen when the signal/noise ratio of the overall spectrum was greater than 12; (4) when the signal/noise of a spectrum was less than 12, the algorithm was less able to distinguish between wavelengths containing information and those containing no information. The probability that an invalid wavelength would be chosen increased as the signal/noise ratio decreased. These trends show that the new row-reduction algorithm is viable as long as the signal/noise ratio of a spectrum is large enough to make any data reduction worthwhile.

B. Methyl Red/Methyl Orange Spectra. The correlation with pH in mixtures of methyl orange and methyl red solution spectra gave statistical correlations ranging from r=0.9798 to r=0.9999, as shown in Table I. These results clearly indicate that the row-reduction algorithm performs well for real solutions where Beer's law is obeyed.

C. Determination of Protein in Wheat. The correlation for protein in wheat is shown in Table II. These results compare well with those obtained by the technique of curve-fitting.[11] It should be noted that the number of samples and the number of wavelengths examined at a time in the row-reduction algorithm are necessarily equal because of the fundamental relationship

TABLE I

Correlation with pH in mixtures of methyl red and methyl orange solutions.

| Chemical system | No. of samples | No. of wavelengths retained | Correlation coefficient (r value) |
|---|---|---|---|
| Methyl red | 4 | 2 | 0.9798 |
| Methyl orange | 4 | 2 | 0.9999 |
| Mixture | 5 | 2 | 0.9934 | of $m$ independent equations for $m$ independent unknowns in linear algebra. The correlation obtained by the row-reduction method using seven wavelengths is shown graphically in FIG. 2; the wavelengths and their respective B coefficients [cf. Eq. (1)] are listed in Table III.

D. Determination of Benzene in Hydrocarbon Mixtures. The correlation for benzene in hydrocarbons is shown graphically in FIG. 3; the wavelengths used and their respective B coefficients are listed in Table IV. The two samples plotted as circles in FIG. 3 were known to be in error because of an inadequate instrumental $N_2$ purge. These latter samples have not been used in calculating the least-squares line, but were retained on the plot to illustrate the possible effect and magnitude of instrumental errors. Although 47 points are plotted in FIG. 3, the precision of the prediction is such that many of the points are not spatially resolvable.

IV. DISCUSSION

A. Computational Efficiency of the Row-reduction Algorithm. The prediction of protein in wheat shown in Table II and FIG. 2 verifies that the row-reduction algorithm is competitive with other regression techniques as far as standard error of prediction is concerned. There are other considerations, however, which favor row-reduction over multilinear regression. One of these considerations is computation time.

TABLE II

Prediction of percent protein in wheat using the row-reduction algorithm

| No. of wavelengths retained for prediction[a] by row-reduction algorithm | No. of samples used both methods | Reliability of predicted percent protein | | | |
|---|---|---|---|---|---|
| | | Row-reduction | | Ref. 11 | |
| | | SEE | SEP | SEE | SEP |
| 2 | 2 | 1.36 | 1.15 | 2.28 | 2.16 |
| 3 | 3 | 0.40 | 0.46 | 2.30 | 2.30 |
| 4 | 4 | 0.38 | 0.38 | 0.243 | 0.30 |
| 5 | 5 | 0.36 | 0.36 | 0.24 | 0.30 |
| 6 | 6 | 0.31 | 0.35 | 0.243 | 0.30 |
| 7 | 7 | 0.27 | 0.26 | 0.14 | 0.15 |

[a]Ref. 11 uses 300 wavelengths for each prediction.

[Fig. 2 redacted]

TABLE III

Seven-wavelength correlation for protein in wheat (see also FIG. 2).

| Wavelength ($\mu$m) | Multiplier (B value) |
|---|---|
| 1.73 | 900.3 |
| 1.74 | −967.6 |
| 1.86 | 5.1 |

TABLE III-continued

Seven-wavelength correlation for protein in wheat (see also FIG. 2).

| Wavelength ($\mu$m) | Multiplier (B value) |
|---|---|
| 1.97 | 34.2 |
| 2.15 | 1.3 |
| 2.17 | 42.9 |
| 2.52 | −18.0 |

TABLE IV

Eight-wavelength correlation for benzene in hydrocarbons (See also FIG. 3).

| Wavelength ($\mu$m) | Multiplier (B value) |
|---|---|
| 2.011 | 0.00073 |
| 2.023 | 0.00971 |
| 2.164 | 0.11889 |
| 2.168 | −0.26828 |
| 2.171 | 0.29825 |
| 2.175 | −0.24175 |
| 2.179 | 0.12348 |
| 2.189 | −0.03678 |

[FIG. 3 redacted]

The number of multiplications and divisions required to solve Eq. (1) for a single matrix is equal to:

$$[-N_u^3 + 3(N_s+1)(N_u)^2 + (3N_s+4)N_u - 6N_s]/6 \quad (11)$$

where $N_u$ is the number of wavelengths in Eq. (1) and $N_s$ is the number of samples in the training set. In turn, the total number of matrices which must be solved to obtain a calibration via row reduction is approximately the total number of wavelengths to be considered ($N_\lambda$) times the number of passes through the wavelength set. Because the number of passes is usually 2, the number of matrices to be solved is ordinarily $2N_\lambda$. Multiplying the number of multiplications and divisions per matrix [Eq. (11)] by the number of matrices ($2N_\lambda$) gives the total number of computations ($N_R$):

$$N_R = [N_\lambda][-N_u^3 + \quad (12)$$

$$3(N_s + 1)(N_u^2) + (3N_s + 4)(N_u - 6N_s]/3$$

The number of multiplications and divisions necessary to obtain a NIRA calibration by "all possible pairs" or "all possible triplets" stepwise regression can be deduced by a two-part computation. The first part is the calculation of the cross terms:

$$\text{No. of cross terms} = \frac{(N_\lambda)(N_\lambda + 1)}{2} \quad (13)$$

Each of these terms is composed of $N_s$ multiplications so the total number of computations for determining the cross terms is:

$$\text{No. of cross term multiplications} = \frac{(N_\lambda)(N_\lambda + 1)(N_s)}{2} \quad (14)$$

The second part of the regression calculation is the inversion of matrices. Each i-by-i matrix inversion requires $i^3$ multiplications and divisions. The number of matrices to be inverted by the all-possible-pairs stepwise regression is $$\frac{(N_\lambda)(N_\lambda - 1)}{2} + 2(N_u - 2)(N_\lambda) \quad (15)$$

The corresponding number for the all-possible-triplets stepwise regression is $$\frac{(N_\lambda)(N_\lambda - 1)(N_\lambda - 2)}{6} + 2(N_u - 3)N_\lambda \quad (16)$$

where both Eqs. (15) and (16) assume one checkback per wavelength addition.

From Eqs. (15) and (16) and the number of multiplications and divisions required to invert each matrix, Eqs. (17) and (18) can be obtained.

No. of calculations in all-possible-pairs stepwise (17)

$$\text{regression} = 4(N_\lambda)(N_\lambda - 1) + 2 \sum_{i=3}^{N_u} i^3(N_\lambda)$$

No. of calculations in all-possible-triplets stepwise (18)

$$\text{regression} = (9/2)(N_\lambda)(N_\lambda - 1)(N_\lambda - 2) + 2 \sum_{i=4}^{N_u} i^3(N_\lambda)$$

An examination of Eq. (12) and Eqs. (14) plus (17) or Eqs. (14) plus (18) gives a semiquantitative basis of comparison of the row-reduction and regression methods. This comparison is tabulated in Table V. It can be observed that row-reduction becomes much more efficient as $N_\lambda \gg N_s$. B. Other Advantages of Row-Reduction. Row-reduction has several advantages over regression other than computational efficiency. These advantages include an increased immunity to baseline drift and to overfitting.

If spectral baseline drift occurs, all wavelengths shift up or down together. Therefore, the offset caused by these shifts can be avoided if the B coefficients of Eq. (1) add to zero. The set of typical B coefficients shown in Table III, calculated by row-reduction, add very nearly

TABLE V

Number of computations for finding the best five and six-wavelength correlations by row-reduction and regression methods.[a]

| No. of wavelengths to search | No. of samples | Regression methods | | Row-reduction |
|---|---|---|---|---|
| | | All possible pairs stepwise | All possible triples stepwise | |
| 19 | 10 | 20 K | 43 K | 12 K |
| 19 | 25 | 21 K | 44 K | 32 K |
| 19 | 50 | 27 K | 51 K | 64 K |
| 140 | 10 | 297 K | 12 M | 90 K |
| 140 | 25 | 446 K | 12 M | 232 K |
| 140 | 50 | 692 K | 13 M | 470 K |
| 700 | 10 | 5.0 M | 515 M | 449 K |
| 700 | 25 | 8.7 M | 519 M | 1.1 M |
| 700 | 50 | 14 M | 525 M | 2.4 M |

[a] $K = \times 10^3$; $M = \times 10^6$.

to zero. This feature is inherent in the row-reduction algorithm and avoids the problem of forcing the sum of the regression coefficients to zero. Regression techniques do not inherently possess this feature.

Overfitting occurs when the solution to Eq. (1) reflects trends in the training sample set that are not present in the prediction set. Row-reduction helps reduce the likelihood of overfitting through its use of only the most orthogonal samples to determine the B coefficients. This selection prevents averaging or diluting the uniqueness of individual samples and forces the prediction to be valid for the most unusual samples in the training set, not for the most "typical" samples.

Finally, row-reduction allows an a priori test for overfitting even if the samples whose constituents are to be predicted have not been chemically determined (i.e., are not part of the training or prediction sets). In particular, if the spectrum of a new sample (at the wavelengths used in Eq. (1)) cannot be formed by some combination of the spectra of the samples used to solve Eq. (1), that sample cannot be accurately predicted. This method for detecting the presence of overfitting will be discussed in a subsequent paper.

V. CONCLUSION

The new row-reduction algorithm appears to be a valid technique for finding the correlation between chemical composition and the absorbance of reflectance spectra for spectrally and chemically complex samples. Row-reduction has the advantages of computational ease and increased resistance to spectral errors compared to regression methods. Finally, row-reduction is conceptually more facile than a multilinear regression, a feature which should aid future research in and interpretation of the NIRA technique.

ACKNOWLEDGEMENTS

This research was supported in part by the Technicon Instrument Corporation, by the Office of Naval Research, and by the National Science Foundation.

1. J. R. Hart, K. H. Norris, and C. Golumbic, Cereal Chem. 39, 94 (1962).
2. D. R. Massie and K. H. Norris, Trans. ASAE 8, 598 (1965).
3. I. Ben-Gera and K. H. Norris, Israel J. Agric. Res. 18, 177 (1968).
4. I. Ben-Gera and K. H. Norris, J. Food Sci. 33, 64 (1968).
5. C. A. Watson, Anal. Chem. 49, 835A (1977).
6. N. R. Draper and H. Smith, *Applied Regression Analysis* (Wiley, New York, 1966).
7. H. Mark, Technicon Instrument Corp., private communication (1982).
8. B. Kolman, *Elementary Linear Algebra*, 2nd ed. (Macmillan, New York, 1977).
9. R. M. Wallace, J. Phys. Chem. 64, 899 (1960).
10. P. C. Williams, K. H. Norris, R. L. Johnsen, K. Standing, R. Fricioni, D. MacAffrey, and R. Mercier, Cereal Foods World 23, 544 (1978).
11. W. R. Hruschka and K. H. Norris, Appl. Spectrosc. 36, 261 (1982).

What is claimed is:

1. A method for quantifying a physical property of a hydrocarbon sample, comprising the steps of:
   (a) determining which wavelengths in the near-infrared spectrum correlate to the physical property to be quantified;
   (b) determining weighting constants which are correlated to the determined wavelength;
   (c) measuring the absorbance of the sample at each of the determined wavelengths; and
   (d) calculating a reference value for the physical property from the measured absorbance of the sample as corrected by the weighting constant.

2. The method of claim 1 wherein the step of calculating the reference value for the physical property comprises calculating:

$$\text{Ref} = \sum_{a=1}^{b} WC(a) \times ABS(a)$$

wherein Ref is the reference value of the physical property to be quantified, b is the number of wavelengths determined to correlate to the physical property, WC(a) is the weighting constant determined to correlate to a wavelength, and ABS(a) is the measured absorbance of the sample at a determined wavelength.

3. The method of claim 1 wherein a row-reduction algorithm is employed to evaluate a field of test data to determine which wavelengths in the near-infrared spectrum statistically correlate to the physical property to be quantified.

4. The method of claim 3 wherein the row-reduction algorithm is employed to evaluate the field of test data to determine the value of the weighting constants for each of the determined wavelengths in the near-infrared spectrum.

5. The method of claim 1 wherein a spectrophotometer is employed to measure the absorbance of the sample at each of the determined wavelengths.

6. The method of claim 1 wherein the physical property to be determined is molecular heat.

7. The method of claim 1 wherein the physical property to be determined is molecular weight.

8. The method of claim 1 wherein the physical property to be determined is methyl groups per molecule.

9. The method of claim 1 wherein the absorbance of the sample is measured by diffuse reflectance.

10. A method of quantifying a plurality of physical properties of a hydrocarbon sample, comprising the steps of:
    (a) selecting separate sets of wavelengths in the near-infrared spectrum which statistically correlate to each of the physical properties to be quantified;
    (b) determining a weighting factor corresponding to each of the selected wavelengths;
    (c) measuring the absorbance of the sample at each of the selected wavelengths; and
    (d) calculating for each physical property being quantified a reference value, the reference value depending upon the measured absorbance of the sample at each wavelength within the corresponding correlated set of wavelengths, and the measured absorbance at each wavelength being corrected by the corresponding weighting constant.

11. The method of claim 10 wherein the step of calculating the reference value for each of the physical properties being quantified comprises calculating:

$$\text{Ref}(m)_1{}^n = \sum_{a=1}^{b} WC(m)(a) \times ABS(m)(a)$$

wherein Ref(m) is the reference value of the physical property being quantified, n is the number of physical properties quantified, b is the number of selected wavelengths within the correlated set of wavelengths corresponding to the physical property being quantified, ABS(m) is the measured absorbance of the gaseous sample at each of the selected wavelengths, and WC(m) is the weighting constant determined to correspond to the selected wavelength at which the absorbance is measured.

12. The method of claim 10 wherein a row-reduction algorithm is used to select the sets of wavelengths in the near-infrared spectrum which statistically correlate to each of the physical properties being quantified.

13. The method of claim 10 wherein row-reduction algorithm is used to determine weighting factors which statistically correspond to each of the selected wavelengths.

14. The method of claim 10 wherein the absorbance of the sample is measured by diffuse reflectance.

15. A method for quantifying a molecular property of a hydrocarbon, comprising the steps of:
    (a) selecting at least two statistically correlated wavelengths in the near infrared spectrum at which to test the hydrocarbon;
    (b) determining weighting factors corresponding to each of the selected wavelengths;
    (c) measuring with a spectrophotometer the absorbance of the hydrocarbon at each of the selected wavelengths; and
    (d) computing a reference value corresponding to the molecular property of the hydrocarbon by correcting with the corresponding weighting factor, and then summing together the measured and weighted absorbances of the hydrocarbon at each of the selected wavelengths.

16. The method of claim 15 wherein the molecular property of the hydrocarbon being quantified is the molecular heat and the step of selecting the statistically correlated wavelengths comprises the step of using a row-reduction algorithm to correlate the selected wavelengths with test data reflecting the true molecular heat of a field of hydrocarbon test samples.

17. The method of claim 15 wherein the molecular property of the hydrocarbon being quantified in the molecular heat and the step of determining the weighting factors comprises the step of using a row-reduction algorithm to correlate the weighting factors with the selected wavelengths and with test data reflecting the true molecular heat of a field of hydrocarbon test samples.

18. The method of claim 15 wherein the selected wavelengths are in the range of 750 to 2500 nanometers.

19. The method of claim 15 wherein four wavelengths are selected, one each at 1701 nanometers, 1958 nanometers, 2150 nanometers and 2181 nanometers.

20. The method of claim 19 wherein the four selected wavelengths have corresponding weighting factors of $-2.9$, $-2.7$, $9.4$ and $-3.8$, respectively.

21. The method of claim 15 wherein the absorbance of the hydrocarbon is measured by diffuse reflectance.

22. The method of claim 15 wherein the molecular property of the hydrocarbon being quantified is the molecular weight and the step of selecting the statistically correlated wavelengths comprises the step of using a row-reduction algorithm to correlate the selected wavelengths with test data reflecting the true molecular weights of a field of hydrocarbon test samples.

23. The method of claim 14 wherein the molecular property of the hydrocarbon being quantified is the molecular weight and the step of determining the weighting factors comprises the step of using a row-reduction algorithm to correlate the weighting factors with the selected wavelengths and with test data reflecting the true molecular weights of a field of hydrocarbon test samples.

* * * * *